United States Patent [19]

Sanchez-Rodarte

[11] Patent Number: 6,016,451

[45] Date of Patent: Jan. 18, 2000

[54] NEUROLOGICAL STABILIZER DEVICE

[76] Inventor: Salvador Sanchez-Rodarte, Mina Del Eden #34 Fracc. Bernales, 98600 Guadalupe, Zacatecas, Mexico

[21] Appl. No.: 09/103,705

[22] Filed: Jun. 24, 1998

[51] Int. Cl.$^7$ .................................................... A61N 1/20
[52] U.S. Cl. ............................................. 607/75; 607/149
[58] Field of Search .................................. 607/72–75, 2, 607/115, 149–151

[56] References Cited

U.S. PATENT DOCUMENTS

| | | | |
|---|---|---|---|
| 5,133,352 | 7/1992 | Lathrop et al. | 607/75 |
| 5,470,349 | 11/1995 | Kleditch et al. | 607/75 |
| 5,607,461 | 3/1997 | Lathrop | 607/75 |

*Primary Examiner*—Jeffrey R. Jastrzab
*Attorney, Agent, or Firm*—Laurence R. Brown

[57] ABSTRACT

This invention relates to a Neurological Stabilizer Device and is directed particularly to provide to the human organism a flux of electric current with the purpose of regulating, in certain cases and circumstances, the natural electric impulses of the human organism, in order to maintain them in a regular average with the objective to stabilize the general condition of the human. This body treatment device has an electrically conductive casing with an internal battery holder compartment arranged for extending conductive wire leads from positive and negative terminals of an internal battery in a manner adapted to contact the skin of a human body and conduct battery current through the body skin. One wire lead forms a latch to hold a battery removably within the compartment. The leads preferably are parallel wires spaced approximately three centimeters apart. A binding harness attaches the device to the body with the wire leads in contact with the skin to conduct battery current. This Neurological Stabilizer Device combines for such purpose, a plurality of components amongst which are included: a positively charged core formed by the combination of a copper casing and an aluminum casing, a positive electrode connected to a primary wire, a negative electrode connected to a secondary wire (part of which is placed inside the aluminum casing), a coil, a capacitor, a battery. To operate the Neurological Stabilizer Device, the positive electrode and the negative electrode, interconnected with the rest of the components are positioned over the skin of the person to be treated, this way, the electric flux originated by the Neurological Stabilizer Device will be transmitted to the body of such person to stimulate and regulate in general the nervous system.

3 Claims, 4 Drawing Sheets

NEUROLOGICAL STABILIZER DEVICE

BACKGROUND OF THE INVENTION

A considerable number of imbalances may be commonly found in the body of any person these days, caused by internal or external factors, due to the consumption of processed foods containing a certain preservative or other substances which, even though they are in the majority of cases approved by food or health authorities, have been shown to interfere in some degree with the neurological functions in the human body; or due to natural pressures in our social, environmental and commercial surroundings which constantly and indisputably provoke considerable tension and stress and which have never been fully studied, evaluated and corrected, with the exception of certain cases such as the invention of the pacemaker to normalize the pulse of the heart or the use of the encephalogram to detect, diagnose and in some cases treat neurological disorders. Apart from these two devices, there has been no practical, simple, effective and economical devices invented in the field of medicine with the specific function of stabilizing the nervous system.

There are unquestionably a large number of medical conditions which result directly from dysfunction of the nervous system caused by internal agents, and triggering as direct secondary effects traumas or diseases of which we may cite as the most important Parkinson's Disease, rheumatoid arthritis, muscular strains, lumbago, sciatic pains, neuralgia, brain disorders, cancer pains and, as far as is known, cellular imbalances which may lead to cancer.

A great deal of research and experimentation with physic physiological tests have been performed with this neurological stabilizer device, involving multiple clinical tests, and it has been concluded as a result that the present invention produces highly favorable results, for which, I am hereby applying for the corresponding patent.

It could be that, as the present invention is explained and analyzed, from the description and accompanying illustrations, new applications arise which result finally in the same effects mentioned above.

DESCRIPTION OF THE INVENTION

PREFERRED EMBODIMENTS OF THE INVENTION

Figure 1:
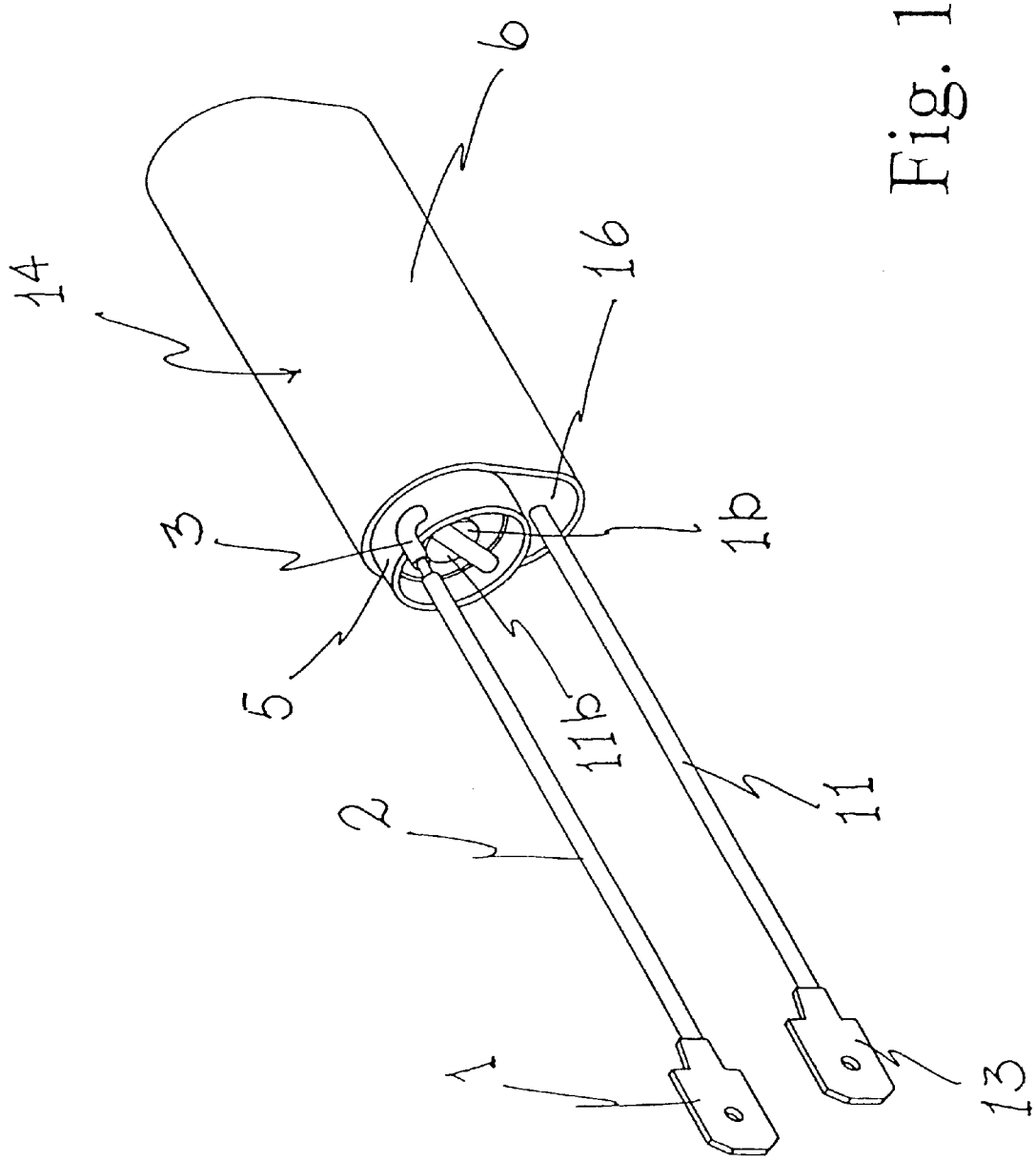
FIG. 1 shows an isometric perspective view of the Neurological Stabilizer Device.
Figure 2:
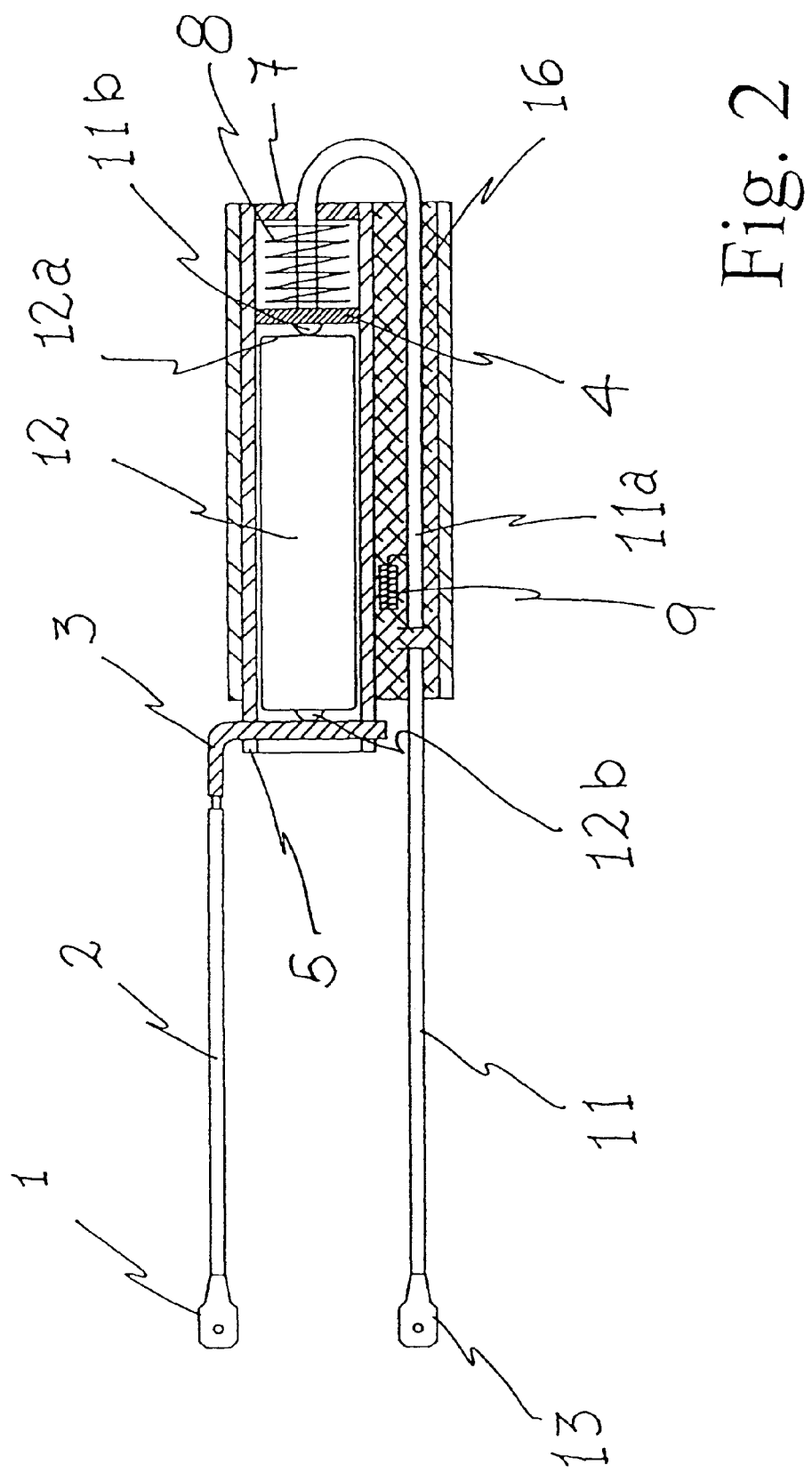
FIG. 2 shows longitudinal sectional view of the Neurological Stabilizer Device.
Figure 3:
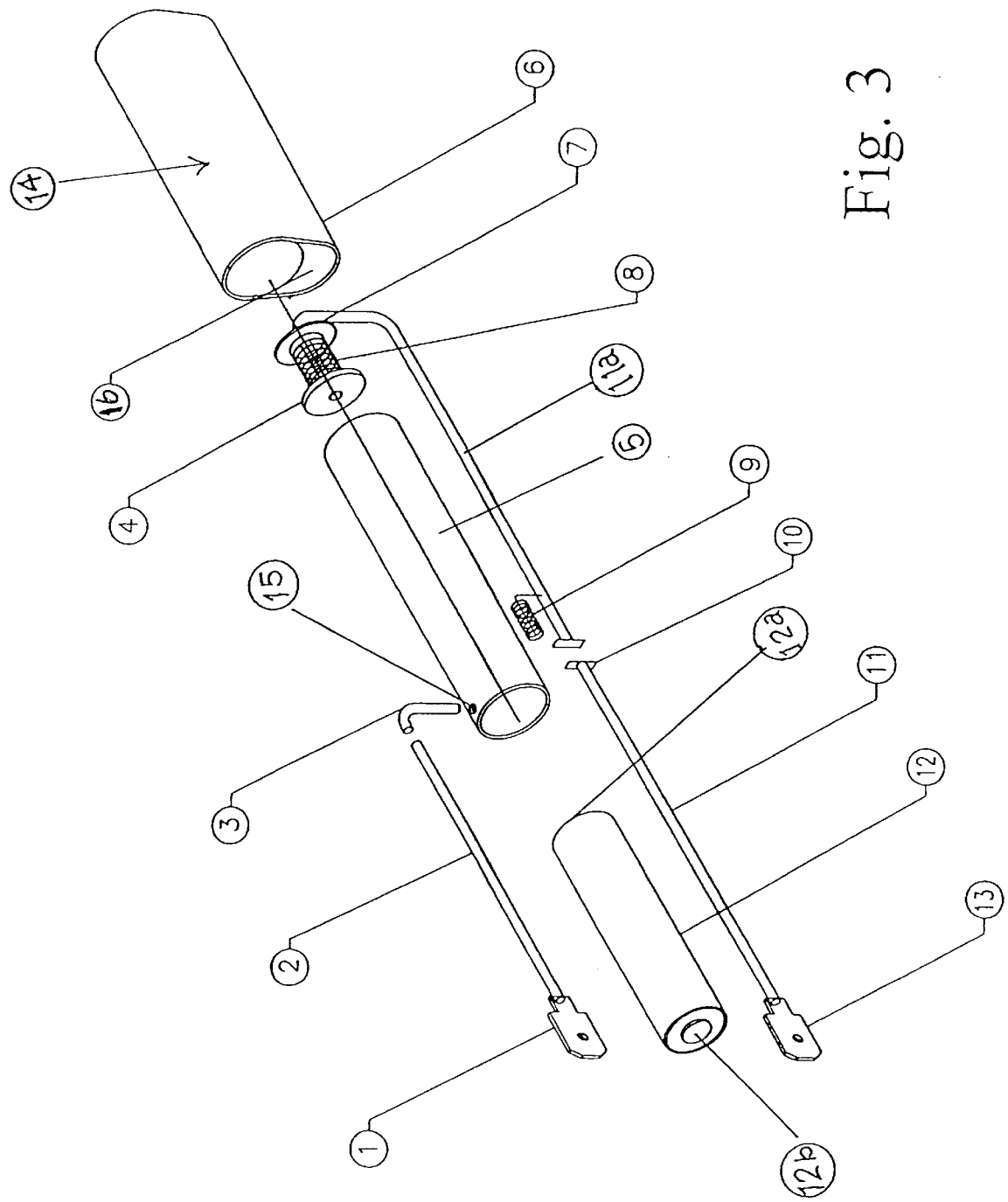
FIG. 3 shows an exploded view of the Neurological Stabilizer Device.
Figure 4:
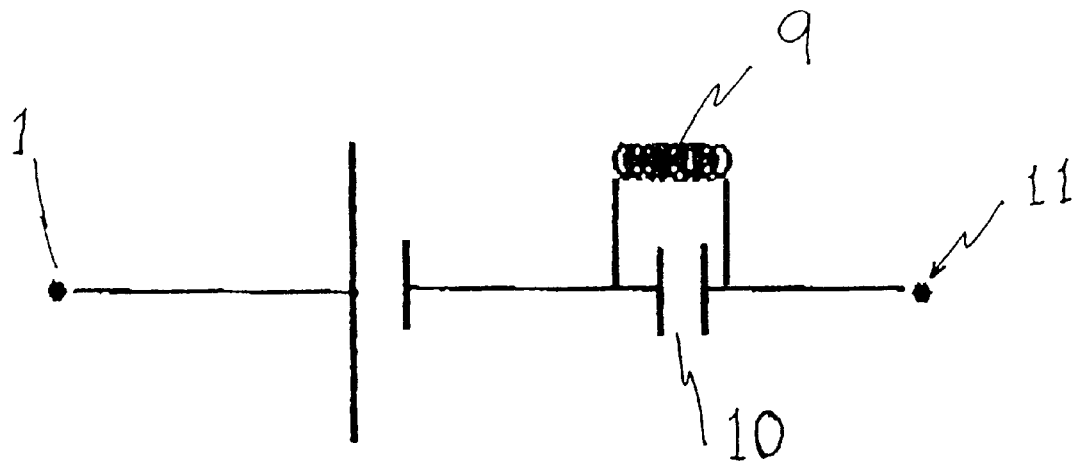
FIG. 4 shows a circuit diagram of the circuitry of the Neurological Stabilizer Device.
Figure 5:
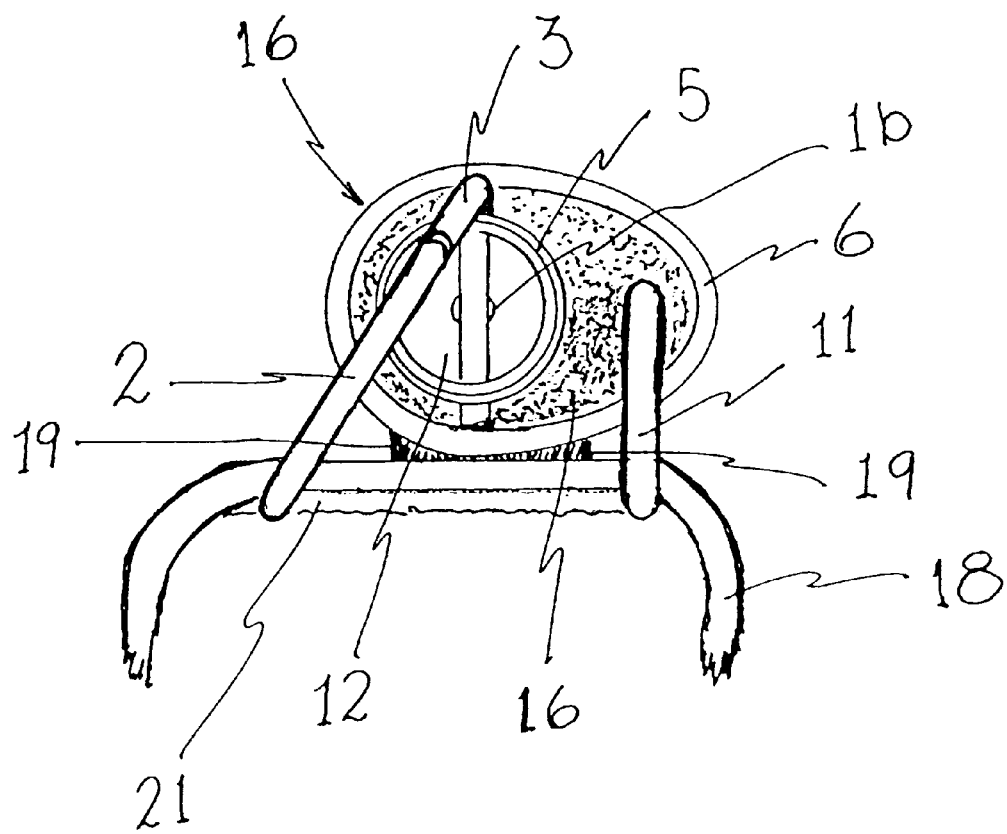
FIG. 5 shows an isometric view of the Neurological Stabilizer Device mounted on a section of a hand and positioned over the skin.

Referring now to the drawings, this Neurological Stabilizer Device comprises in combination a copper casing (5), inside of which the battery (12) with a capacity of 1.5 volts is inserted, and an aluminum casing (6), inside of which the copper casing (5) is located. Both, the copper casing (5) and the aluminum casing (6) form the positively charged case. Inside the aluminum casing (6) the posterior section (11a) of the secondary wire (11), the tail (7), the spring (8), the coffer (4), the coil (9), and the capacitor (10) are positioned. When this positioning has been done, a seal (16), preferably manufactured of a polyester resin is poured inside the aluminum casing (6), embedding each and every one of the components located inside of the aluminum casing (6).

During the process of positioning inside the aluminum casing (6), the terminal (11b) of the secondary wire (11) penetrates across the tail (7), the spring (8) and the cover (4) to which such terminal (11b) is attached; in such position, the terminal (11b) will be always in condition to be in contact with the base (12a) (negative pole) of the battery (12).

This Neurological Stabilizer Device comprises also in combination a positive electrode (1) which is interconnected by the primary wire (2) to a pin (3), which, once the battery (12) has been inserted into the copper casing (5), such pin (3) is introduced across the orifices (15) located on the front end of the copper casing (5), this way the pin (3) operates as a hook to keep the battery (12) firmly positioned inside the copper casing (5), and also functions as a connector between the positive terminal (12b) of the battery (12) transmitting this way the electric current to both, the copper casing (5) and, the aluminum casing (6) forming a positively charged core current, connected to the positive electrode (1) by the primary wire (2), and to the negative electrode (13) by the secondary wire (11).

In order to maintain a constant contact between the base of the battery (12)(negative pole) and the terminal (11b) of the secondary wire (11), between the cover (4) and the tail (7), there is a spring (8) which exerts constant pressure over the cover (4), while the battery (12) remains inserted inside the copper casing (5).

Along the circuit of the Neurological Stabilizer a coil (9) rated at 10 microhenries is incorporated, the function of such component is to operate as a screen that, in combination with the capacitor (10), will neutralize, avoid or stop, any circuit leaks; this way said leaks do not interfere with the function of the stabilizer, and the current will follow the intended course in order to reach and stabilize the nervous system in the human body.

MANNER OF OPERATION

In order to get the Neurological Stabilizer Device in operation, it is necessary that both electrodes, positive (1) and negative (13), be positioned in contact with the skin (21) of the person using the stabilizer; it is recommended that the distance between the electrodes remains approximately around three (3) centimeters; for the purpose of position the neurological stabilizer, a fastening band or any other type of binder (18) should be affixed to the positively charged casing (14); once the stabilizer has been placed on the chosen place of the human body and the electrodes (1, 13) positioned the skin will operate as a bridge of transmission between the electrodes.

The Neurological Stabilizer Device may operate on the wrist, the chest, the waist, the leg, the ankle, the neck or any other part of the body where it may be practical to wear it, as far as electrodes (1, 13), remain with a separation of approximately 3 (three) centimeters between them.

As stated before, When the stabilizer is positioned in operation, in a matter of seconds the electrical current of the stabilizer starts to combine with the electrical impulses of the nervous system. It has been proved and demonstrated in multiple experiments of scientific type that the nervous system stabilizes producing certain beneficial effects which conduct to avoid or alleviate sickness such as: Parkinson, arthritis, rheumatism, muscular tension, lumbago, neuralgia, neuropathy and cancer pains.

What is claimed is:

1. A human body treatment device comprising in combination, a battery, a battery holder compartment, a casing of conductive material enveloping the battery holder compartment containing said battery, two spaced conductive electrode wires coupled to respective positive and negative electrodes of said battery to extend outside said casing in a position for contacting human body skin to thereby conduct current internally into the human body, one said spaced conductive electrode wire being configured as a removable latch for confining the battery within said battery holder compartment.

2. The device defined in claim 1 further comprising binding means affixed to said casing for holding said electrodes on said human body in contact with said skin.

3. The device defined in claim 1 wherein the casing of conductive material is electrically connected to said battery positive terminal.

* * * * *